(12) United States Patent
Cheng (10) Patent No.: US 10,100,941 B2
(45) Date of Patent: Oct. 16, 2018

(54) VALVE POSITIONING STRUCTURE

(71) Applicant: Mei-Li Cheng, Taipei (TW)

(72) Inventor: Mei-Li Cheng, Taipei (TW)

( * ) Notice: Subject to any disclaimer, the term of this patent is extended or adjusted under 35 U.S.C. 154(b) by 105 days.

(21) Appl. No.: 14/429,770

(22) PCT Filed: Oct. 10, 2013

(86) PCT No.: PCT/CN2013/084970
§ 371 (c)(1),
(2) Date: Mar. 19, 2015

(87) PCT Pub. No.: WO2014/059892
PCT Pub. Date: Apr. 24, 2014

(65) Prior Publication Data
US 2015/0233485 A1 Aug. 20, 2015

(30) Foreign Application Priority Data
Oct. 19, 2012 (CN) .......................... 2012 1 0399435

(51) Int. Cl.
*F16K 1/00* (2006.01)
*F16K 1/52* (2006.01)
(Continued)

(52) U.S. Cl.
CPC ............ *F16K 15/20* (2013.01); *A61B 5/0235* (2013.01); *A61M 25/10185* (2013.11);
(Continued)

(58) Field of Classification Search
CPC . F16K 1/00; F16K 1/304; F16K 1/306; F16K 1/52; F16K 11/00; F16K 11/0025;
(Continued)

(56) References Cited

U.S. PATENT DOCUMENTS 1,314,195 A * 8/1919 Jarvis .................... F16K 35/025
222/474
1,494,890 A * 5/1924 Colburn ............ F16K 31/52408
137/556
(Continued)

FOREIGN PATENT DOCUMENTS

EP 0014977 A1 * 9/1980 ........... A61B 5/0235
EP 0306897 A2 * 3/1989 ........... H01H 13/705
(Continued)

*Primary Examiner* — Reinaldo Sanchez-Medina
*Assistant Examiner* — Hailey K Do
(74) *Attorney, Agent, or Firm* — Leong C. Lei (57) ABSTRACT

A valve positioning structure is provided for pressing down a switch arranged in a valve so that fluid is allowed to flow through an inlet opening of the valve when the switch is pressed down in order to control the fluid to flow into/out of at least one bladder. The valve positioning structure includes a casing that receives the valve therein and the casing is provided with a contact member and a manipulation member respectively and movably on upper and lower surfaces of the casing. The contact member and the manipulation member are coupled to each other so that the contact member is operable to drive the manipulation member to move. The manipulation member includes an operation section, where the operation section is movable toward and is enabled to press down the switch when the manipulation member is driven by the contact member to move toward the switch.

16 Claims, 11 Drawing Sheets

(51) Int. Cl.
*F16K 31/524* (2006.01)
*A61B 5/02* (2006.01)
*A61M 39/22* (2006.01)
*A61M 25/10* (2013.01)
*F16K 15/20* (2006.01)
*A61B 5/0235* (2006.01)

(52) U.S. Cl.
CPC ............ *A61M 39/22* (2013.01); *F16K 1/00* (2013.01); *F16K 1/52* (2013.01); *F16K 31/524* (2013.01); *F16K 31/52408* (2013.01); *Y10T 137/3584* (2015.04); *Y10T 137/6103* (2015.04)

(58) Field of Classification Search
CPC .......... F16K 11/04; F16K 11/20; F16K 11/22; F16K 21/04; F16K 31/44; F16K 31/524; F16K 31/52408; F16K 31/52416; F16K 35/022; F16K 35/025; F16K 35/14; F16K 31/52; F16K 31/523; F16K 31/52475; F16K 31/52483; A61B 5/0235; A61M 39/22; A61M 4/1408; A61M 2230/30; A61M 25/10185; A61M 25/10184; A61M 39/223; A61M 39/28; A61M 39/286; A61M 39/287; A61M 2039/224; Y10T 137/3677; Y10T 137/6103; Y10T 137/7069; Y10T 137/7131; Y10T 137/7162; Y10T 137/7225; Y10T 137/7144; Y10T 137/86549; Y10T 137/86558; Y10T 137/86831; Y10T 137/86895; Y10T 137/87016; Y10T 137/87161; Y10T 137/87153; Y10T 137/87571; Y10T 137/87708; Y10T 137/87584; Y10T 137/57692; Y10T 137/87837
USPC .......... 70/175, 176, 179; 251/228, 230, 101, 251/102, 104–106, 110, 111, 113, 89, 251/89.5, 251–263
See application file for complete search history.

(56) References Cited

U.S. PATENT DOCUMENTS

| | | | | |
|---|---|---|---|---|
| 2,716,998 | A * | 9/1955 | Knasko | B60S 5/043 137/231 |
| 3,220,695 | A * | 11/1965 | Jones | E03C 1/23 251/230 |
| 3,254,671 | A * | 6/1966 | Berliner | A61B 5/0235 137/565.12 |
| 3,751,000 | A * | 8/1973 | Natkanski | A61B 5/0235 137/583 |
| 3,954,099 | A * | 5/1976 | Raczkowski | A61B 5/0235 137/556 |
| 4,227,548 | A * | 10/1980 | Botnick | F16K 11/20 137/606 |
| 4,852,551 | A * | 8/1989 | Opie | A61B 1/00068 137/595 |
| 5,496,169 | A * | 3/1996 | Chen | F23Q 3/00 431/153 |
| 5,573,034 | A * | 11/1996 | Gabrlik | F16K 11/0655 137/625.25 |
| 6,935,536 | B2 * | 8/2005 | Tardif | A47J 41/0027 222/153.14 |
| 7,093,609 | B2 * | 8/2006 | Chen | F04B 33/005 137/223 |
| 2008/0023577 | A1 * | 1/2008 | Zhen | B05B 1/1618 239/449 |
| 2008/0029374 | A1 * | 2/2008 | Christopher | H01H 25/00 200/329 |
| 2008/0066810 | A1 * | 3/2008 | Barak | A61M 39/22 137/493.8 |

FOREIGN PATENT DOCUMENTS

| | | | | |
|---|---|---|---|---|
| GB | | 471254 A * | 9/1937 | ....... F16K 31/52408 |
| WO | WO 0119449 A1 * | | 3/2001 | .......... A61M 5/1408 |

* cited by examiner

VALVE POSITIONING STRUCTURE

TECHNICAL FIELD OF THE INVENTION

The present invention relates generally to a valve positioning structure.

DESCRIPTION OF THE PRIOR ART

An inflatable mat that allows for charging/discharging air therein/therefrom is often connected to a valve, which comprises a switch. To use, an opening of air chamber formed in the valve is opened or closed as being controlled by the switch pressed down or not so that the valve may control ingress and egress of air into and from the inflatable mat.

A user, when operating the valve, must keep on pressing down the switch of the valve with one hand thereof in order to keep the opening of the valve widely open to allow air to flow into or out of the valve. This often causes soreness and tiredness of the hand of the user. Further, the opening/closing of the valve is controlled based on the sensation of the hand and such control is generally unreliable and unstable, making it not possible to have air to flow in a quantitative and stable manner into or out of the inflatable mat.

In view of the above problems, the present invention aims to provide a solution to address the above-discussed technical issue.

SUMMARY OF THE INVENTION

An object of the present invention is to provide a valve positioning structure that keeps a valve switch persistently pressed down in order to maintain a valve opening in an open condition.

To achieve the above object, the present invention provides the following solution:

A valve positioning structure is provided for pressing down a switch arranged in a valve so that a fluid is allowed to flow through an inlet opening of the valve when the switch is pressed down in order to control the fluid to flow into/out of at least one bladder. The valve positioning structure comprises a casing that receives and houses the valve therein and the casing is provided with a contact member and a manipulation member respectively and movably on upper and lower surfaces of the casing. The contact member and the manipulation member are coupled to each other so that the contact member is operable to drive the manipulation member to move. The manipulation member comprises an operation section, where the operation section is movable toward and is enabled to press down the switch when the manipulation member is driven by the contact member to move toward the switch.

The casing comprises an opening and the opening extends outside the casing.

The casing comprises a guide hole of a predetermined length formed therein. The contact member comprises a coupling element corresponding to the guide hole. The coupling element is received in the guide hole and is movable along the guide hole. The manipulation member is coupled to the coupling element to be connected to the contact member, whereby the manipulation member is drivable by the contact member to move along the guide hole toward the switch.

The casing comprises two through holes of a predetermined length formed therein. The contact member comprises guiding elements corresponding to the through holes. The guiding elements are respectively received in the through holes and movable along the through holes.

The contact member comprises a surface on which a plurality of projections for receiving a finger to touch and press thereon.

The contact member comprises a bearing section formed thereon to receive a finger to contact and push.

The operation section of the manipulation member is of a C shape and the operation section has two side parts each having an underside that comprises a pressing section. The pressing section has a lower horizontal surface and a slope surface connected to the lower horizontal surface, whereby when the manipulation member is moved toward the switch, the slope surface of the pressing section reduces a resistance against impact on the switch so as to have the slope surface and the lower horizontal surface of the pressing section raised up to reach atop the switch for inducing an operation of pressing down the switch.

That the operation section of the manipulation member is of a C shape and the operation section has two side parts each comprising a projecting rim to constrain the movement of the manipulation member in a direction toward the switch.

The contact member is rotatably mounted to the casing by a pivot like coupling element and the contact member and the manipulation member are coupled together by the coupling element, whereby when the contact member is rotated, the manipulation member is rotatable in unison therewith.

The operation section is formed on an underside of the manipulation member and comprises a raised arcuate surface, whereby when the manipulation member is rotated toward the switch, the arcuate surface of the operation section reduces a resistance against impact on the switch to have the operation section raised up to reach atop the switch for inducing an operation of pressing down the switch.

With the above arrangement, the present invention allows the contact member to be operated in such a way as to cause the manipulation member to move toward the switch in order to achieve persistent pressing of the switch for keeping the inlet opening of the valve open to allow fluid to flow in and out of the valve in a quantitative and stable manner. A user can keep the inlet opening of the valve open to allow the fluid to flow into and out of the bladders in a quantitative and stable manner without persistently placing a finger on and pressing down the switch of the valve.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 2:
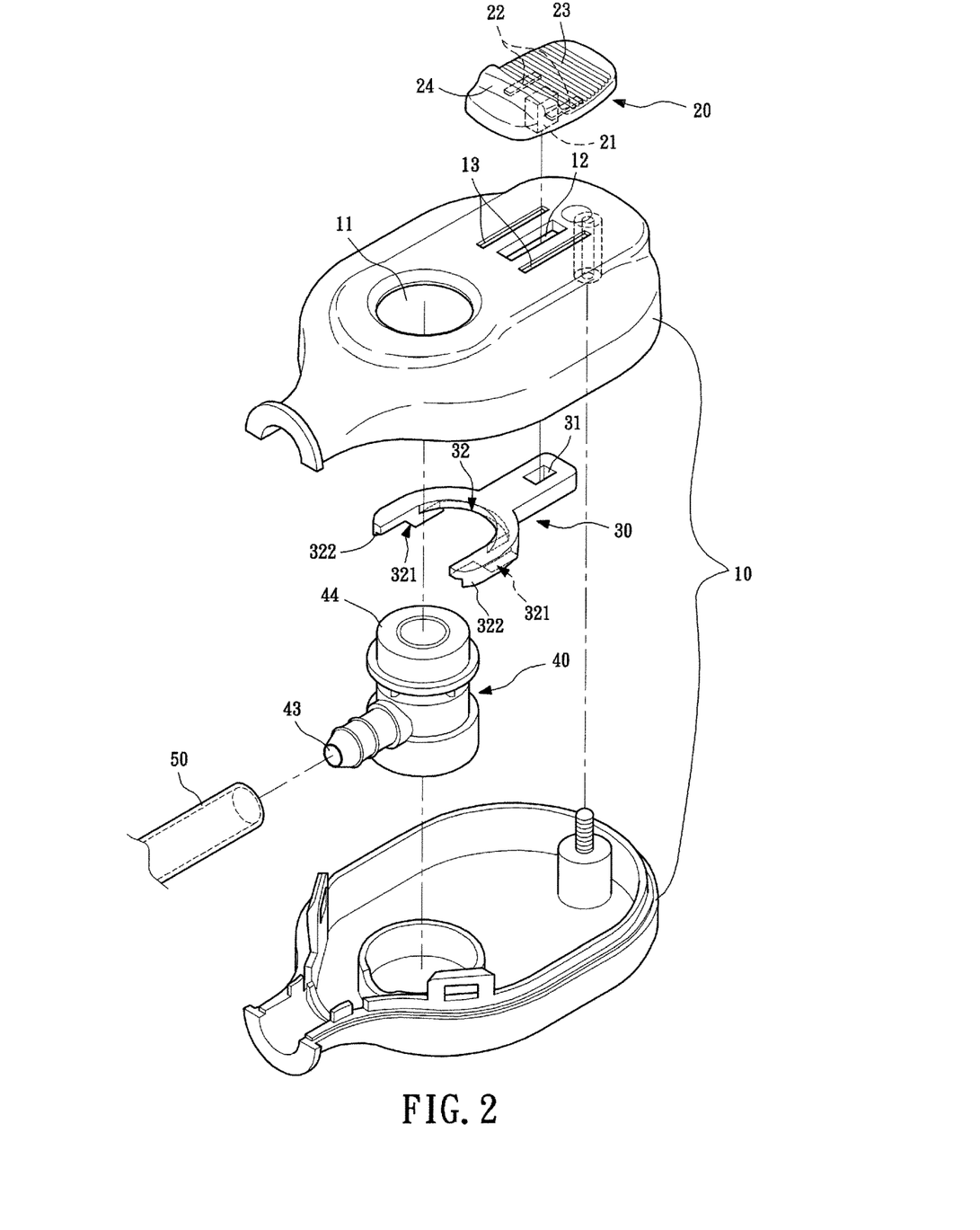
FIG. 2 is an exploded view of the present invention.
Figure 6:
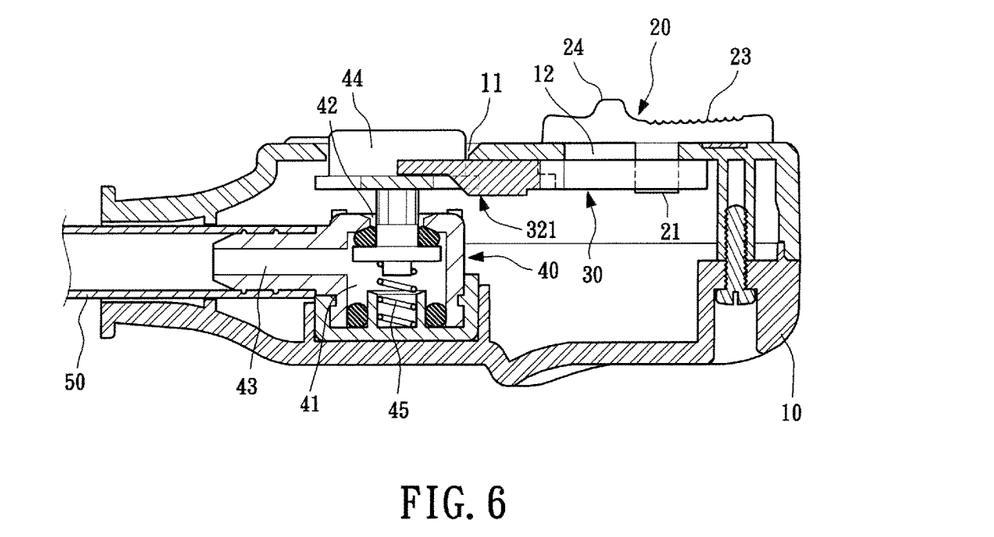
FIG. 6 is a cross-sectional view of the present invention.
Figure 8:
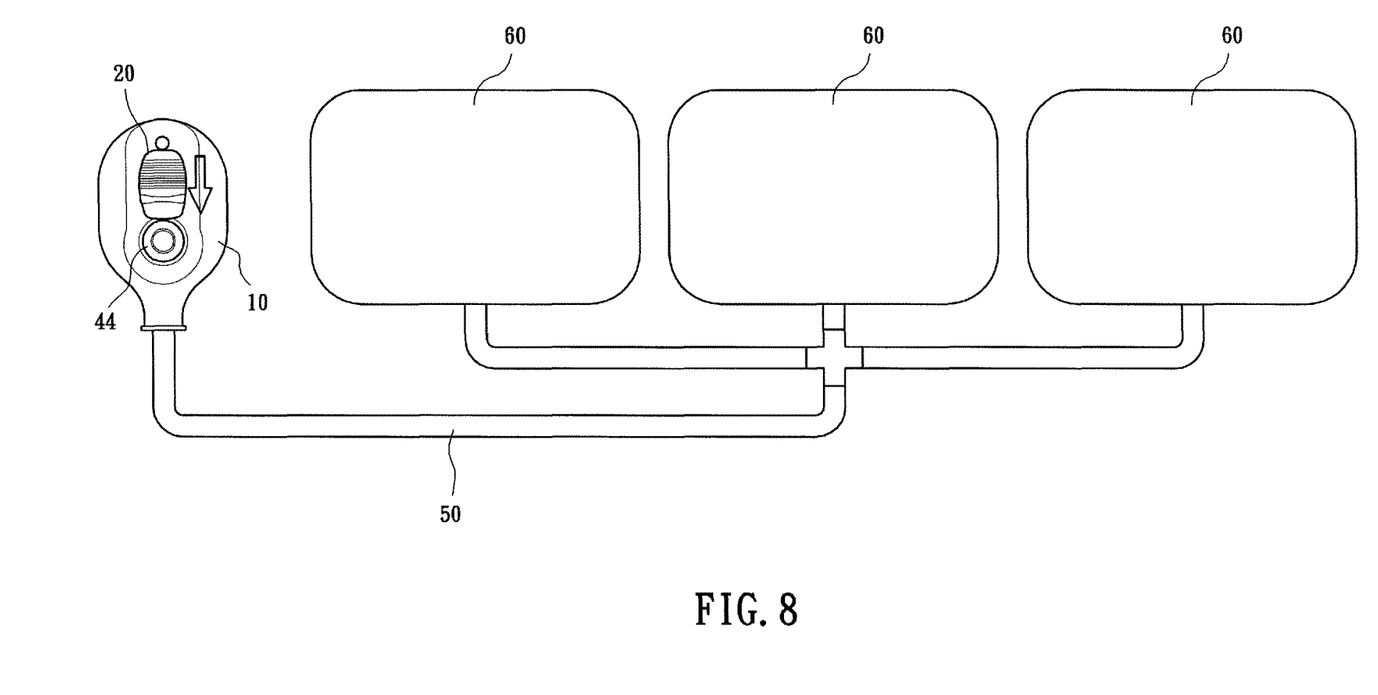
FIG. 8 is a schematic view illustrating the present invention connected to bladders.

Referring to FIGS. 2, 6, 8, a valve 40 comprises, structurally, a flow chamber 41, an inlet opening 42, and an outlet opening 43 that are in communication with each other. The outlet opening 43 is connected to a connection tube 50 and the connection tube 50 is connected to a plurality of bladders 60 so that the valve 40 is operable to control ingress and egress of fluid into and out of the bladders 60. A switch 44 has a part received in the flow chamber 41 and another part of the switch 44 is set to extend through the inlet opening 42 to have an upper end thereof projecting outside a surface of the valve 40 to allow a hand of a user to selectively press down the switch 44. An elastic body 45 is arranged under the switch 44 to push and elastically bias the switch 44 upward so as to have the switch 44 close the inlet opening 42, whereby when the switch 44 is pressed down, the inlet opening 42 is opened and the elastic body 45 is compressed to accumulate a spring force for re-positioning the switch 44 so that when the external force pressing down the switch 44 is removed, the spring force of the elastic body 45 is released to have the switch 44 re-close the inlet opening 42.

Figure 1:
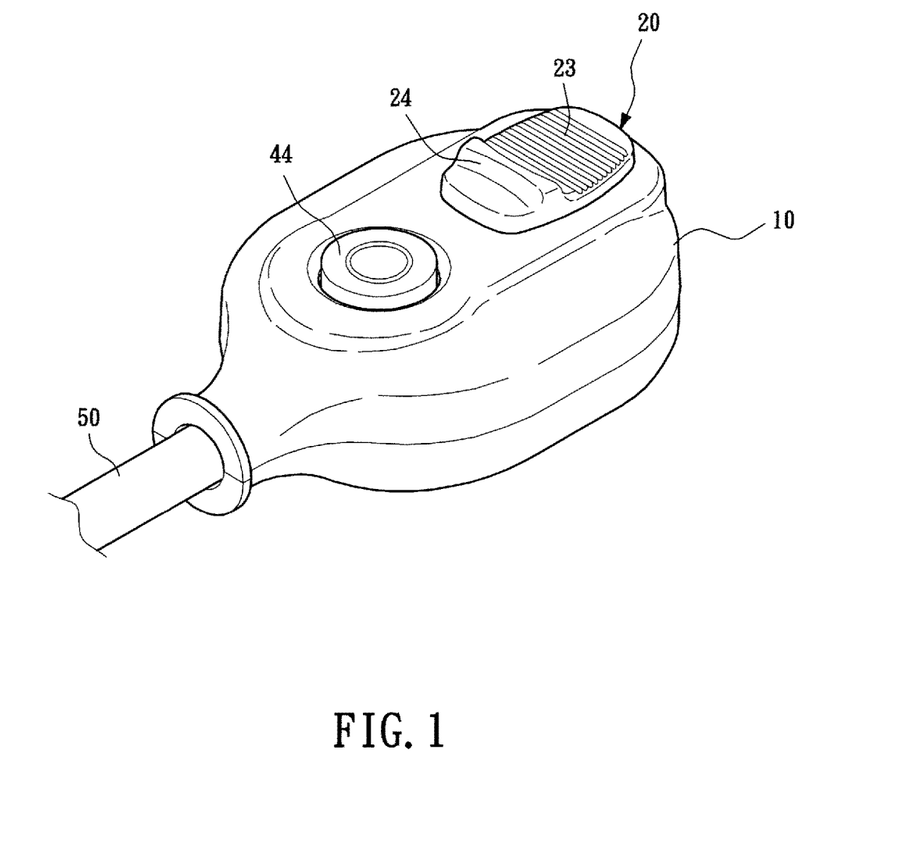
FIG. 1 is a perspective view of the present invention.

Referring to FIGS. 1 and 2, a preferred embodiment of the present invention comprises a casing 10 and a contact member 20 and a manipulation member 30 mounted to and in the casing 10 and in operatively coupling with each other. The casing 10 receives therein and houses the valve 40. The contact member 20 is movable in such as way as to drive the manipulation member 30 to move toward the switch 44 to achieve a position to maintain pressing down the switch 44, so as to persistently keep the inlet opening 42 of the valve 40 open, allowing a fluid to flow in and out of the valve 40 in a quantitative and stable manner.

Referring to FIGS. 2, 3, 4, and 6, the casing 10 of the present invention can be composed of upper and lower casing members that define therein an interior space for receiving and accommodating the valve 40. The casing 10 comprises an opening 11, wherein the opening 11 allows an upper part of the switch 44 to project outside the casing 10. The casing 10 helps protect and beautify the valve 40 and enables gripping by the hand of the user for easily and efficiently pressing down the switch 44. The casing 10 has an upper surface in which a guide hole 12 of a predetermined length and two through holes 13 arranged on opposite sides of the guide hole 12 and having a predetermined length are formed. The guide hole 12 and the through holes 13 serve as rails for the movement of the contact member 20 and also functions to limit the distance of the movement of the contact member 20.

The contact member 20 has a lower surface positioned on the upper surface of the casing 10 and the lower surface of the contact member 20 is provided with a coupling element 21 and two guiding elements 22 respectively corresponding to the guide hole 12 and the through holes 13. The coupling element 21 and the guiding elements 22 are respectively received in the guide hole 12 and the through holes 13 and are movable therein. The contact member 20 has an upper surface that is provided with a plurality of projections 23 and a bearing section 24. The projections 23 are arranged to receive a finger to contact and press and to increase a frictional force therebetween. The bearing section 24 is provided to receive the finger to contact and push so that the finger may push and move the contact member 20.

The manipulation member 30 has an upper surface that is positioned against an upper inside surface of the casing 10. The manipulation member 30 has an end in which a coupling hole 31 is formed to receive the coupling element 21 to fit therein and couple thereto so that the contact member 20 and the manipulation member 30 are mounted to the casing 10 and are movable along the guide hole 12 and the through holes 13 toward the switch 44. The manipulation member 30 comprises a C-shaped operation section 32. The operation section 32 has two side parts each having an underside that comprises a pressing section 321. The pressing section 321 comprises upper and lower horizontal surfaces and a slope surface connecting between the upper and lower horizontal surfaces. When the manipulation member 30 is not moved toward the switch 44 yet, the upper horizontal surface of the pressing section 321 is set on a circumferential flange of the switch 44; and when the manipulation member 30 is moved toward the switch 44, the lower horizontal surface of the pressing section 321 presses down the circumferential flange of the switch 44. Since the operation section 32 is of a C shape of which the two side parts are provided with projecting rims 322, when the manipulation member 30 is being moved toward the switch 44, the operation section 32 surround a major portion of the circumferential flange of the switch 44 to provide an effect of constraint so that the manipulation member 30 is constrained to move in a direction toward the switch 44 without any error caused by deviation of the movement.

Figure 3:
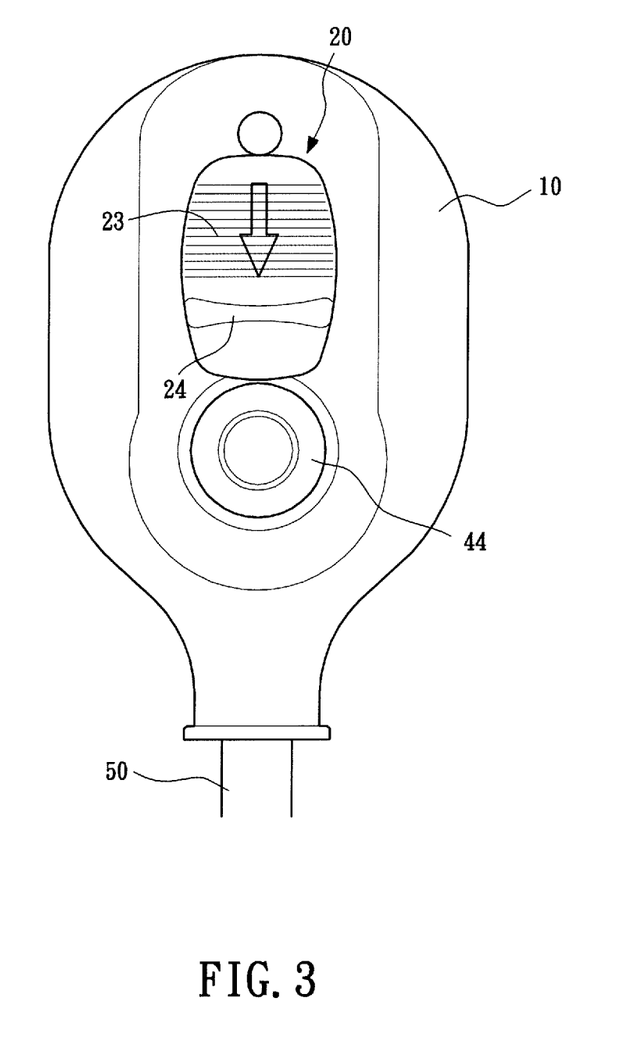
FIG. 3 is a top plan view illustrating a movement of a contact member according to the present invention.
Figure 4:
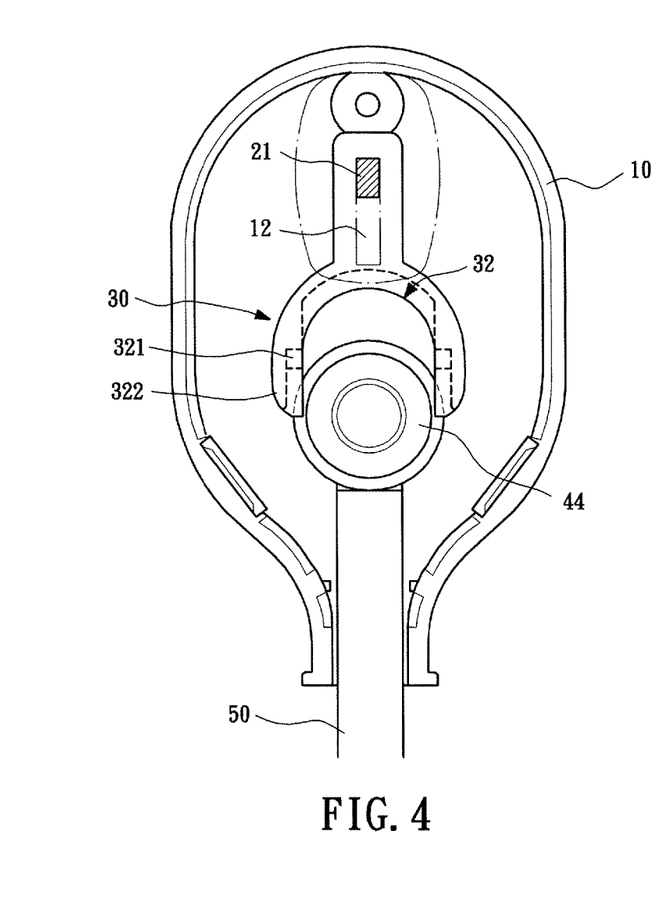
FIG. 4 is a top plan view illustrating an interior structure inside a casing of the present invention.
Figure 5:
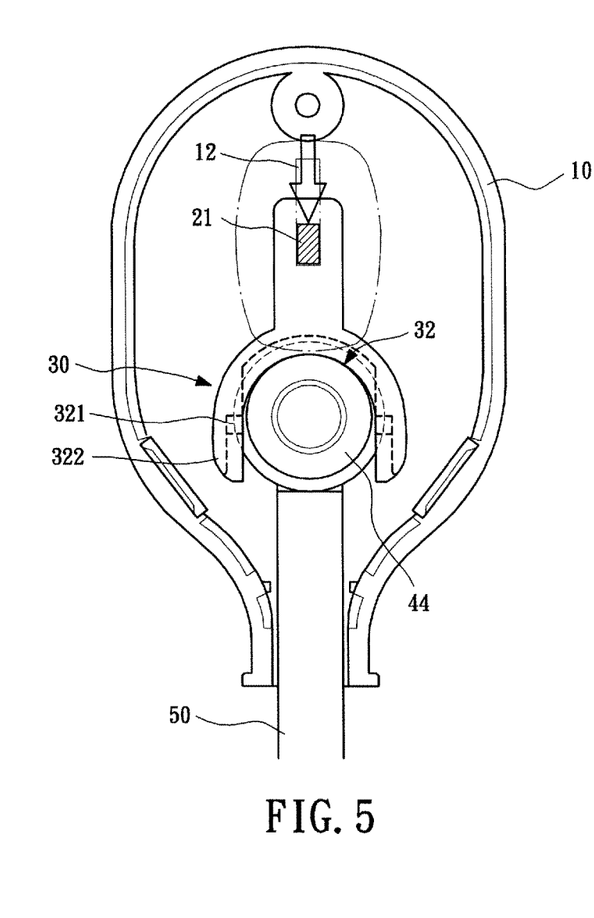
FIG. 5 is a top plan view illustrating a movement of a manipulation member and also showing the interior structure inside the casing of the present invention.
Figure 7:
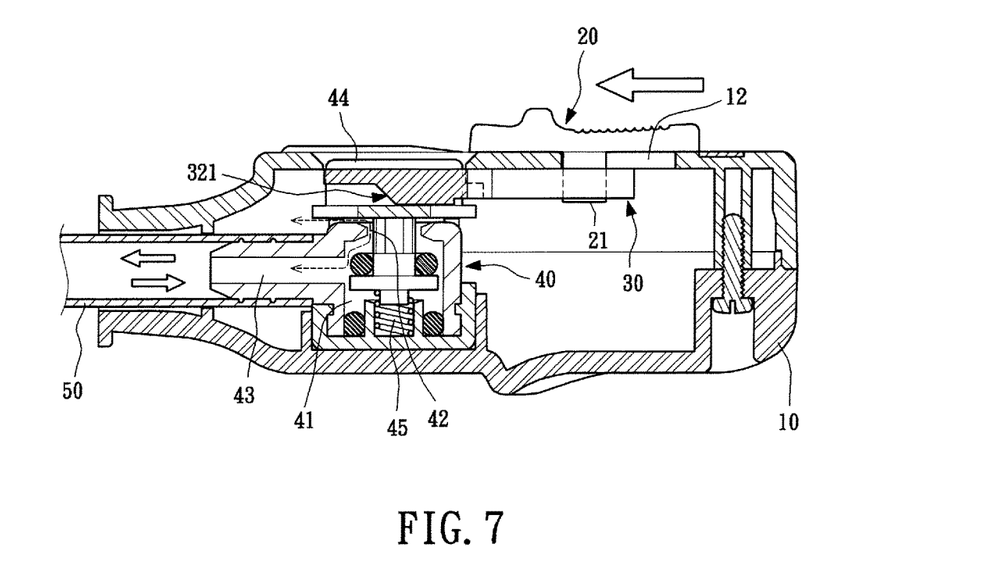
FIG. 7 is a cross-sectional view illustrating an operation of the present invention.

Referring to FIGS. 3, 5, and 7, to operate the present invention, a finger touches and pushes and moves the contact member 20 and the manipulation member 30 is caused to move, in unison therewith, toward the switch 44 of the valve 40. During the movement, the manipulation member 30 uses the slope surfaces of the pressing sections 321 to reduce the resistance resulting from impact against the circumferential flange of the switch 44 so as to allow the slope surface and the lower horizontal surface of the pressing section 321 to be easily raised up and reaching atop the circumferential flange of the switch 44 thereby inducing an operation of pressing down the switch 44. As such, the user does not need to use the finger to persistently press down the switch 44 of the valve 40 and the inlet opening 42 of the valve 44 is kept open to allow the fluid to flow in and out of the bladders 60 in a quantitative and stable manner (see FIG. 8).

Figure 9:
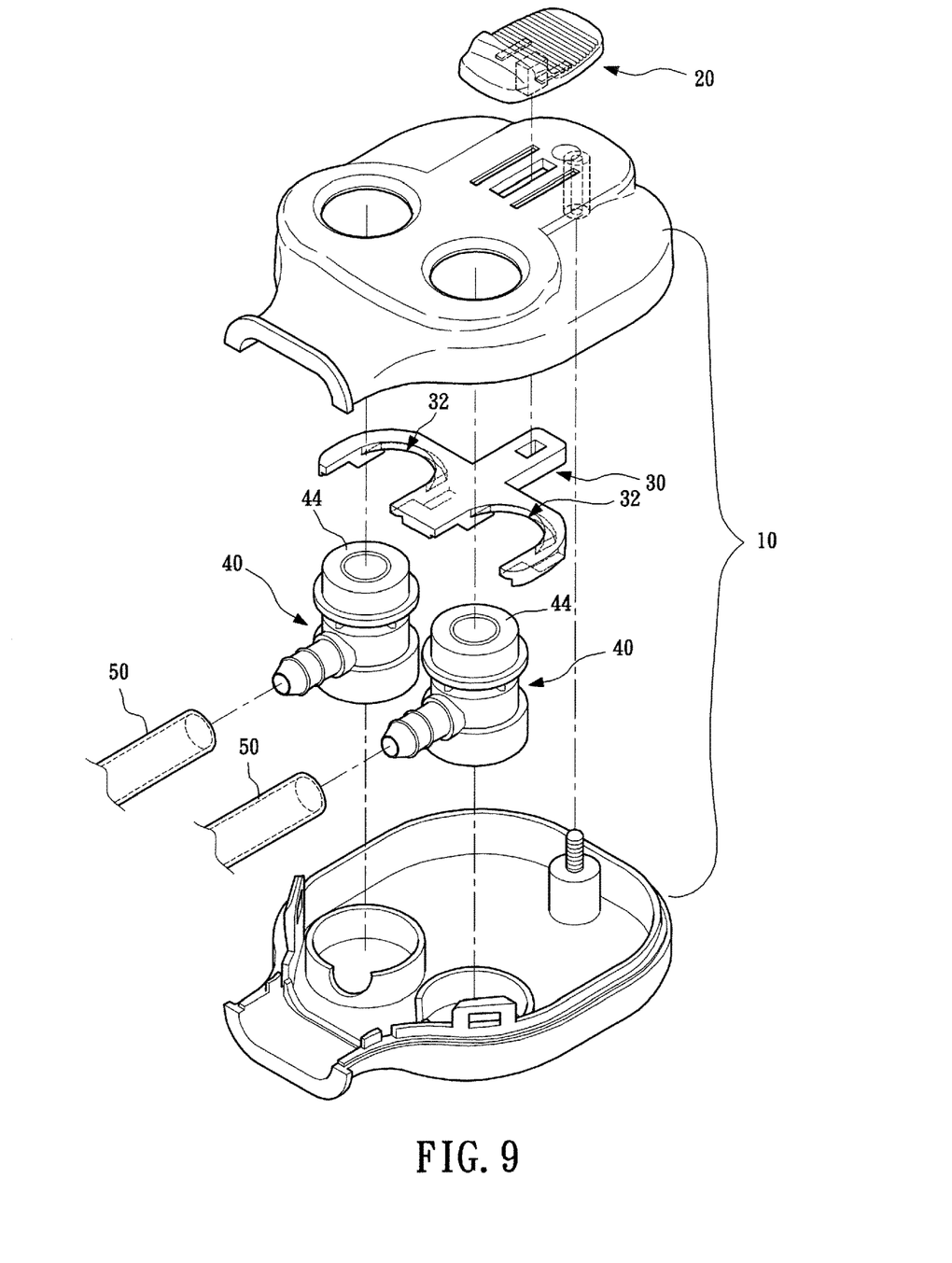
FIG. 9 is an exploded view showing anther embodiment of the present invention.
Figure 10:
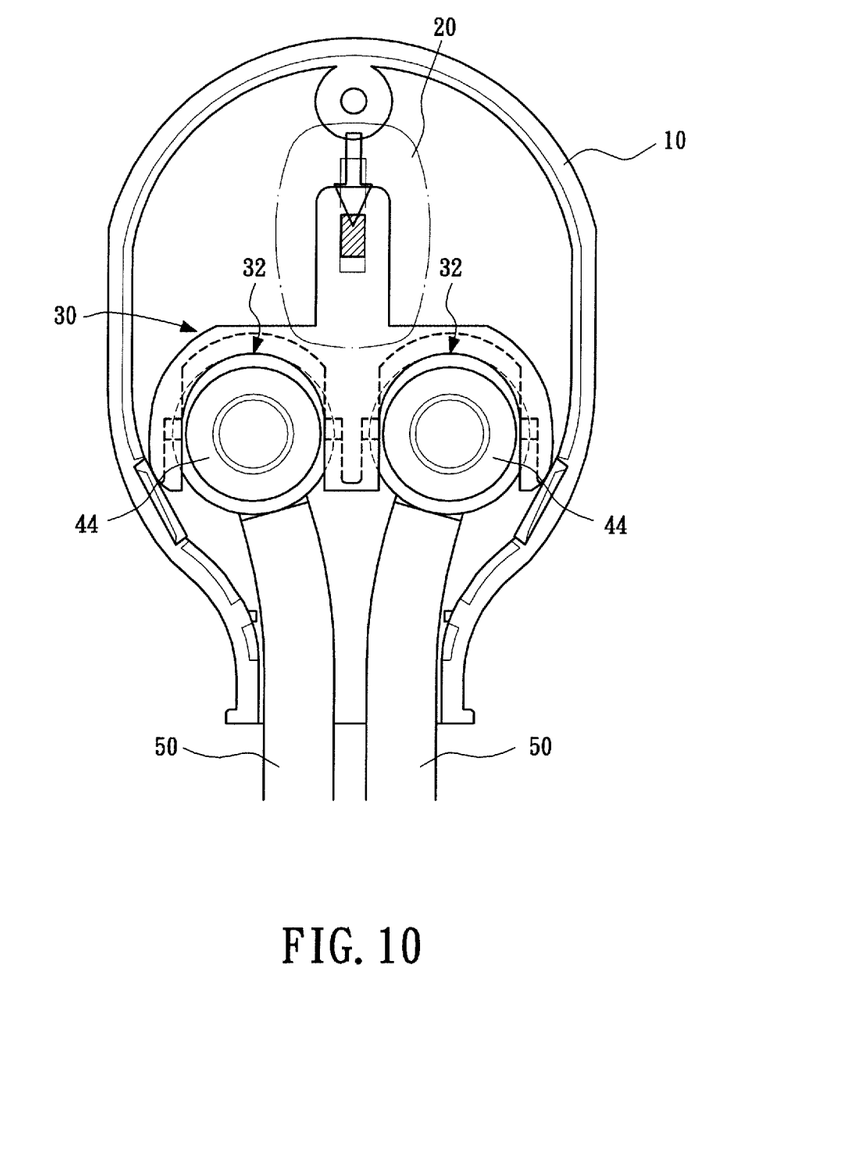
FIG. 10 is a top plan view illustrating the movement of the manipulation member and also showing the interior structure inside the casing of said another embodiment of the present invention.

Referring to FIGS. 9 and 10, when two such valves 40 are used together, it only needs to change the number of the operation section 32 to two. As such, when the contact member 20 is pushed and moved, the manipulation member 30 can simultaneously press down the switches 44 of the two valves 40.

Figure 11:
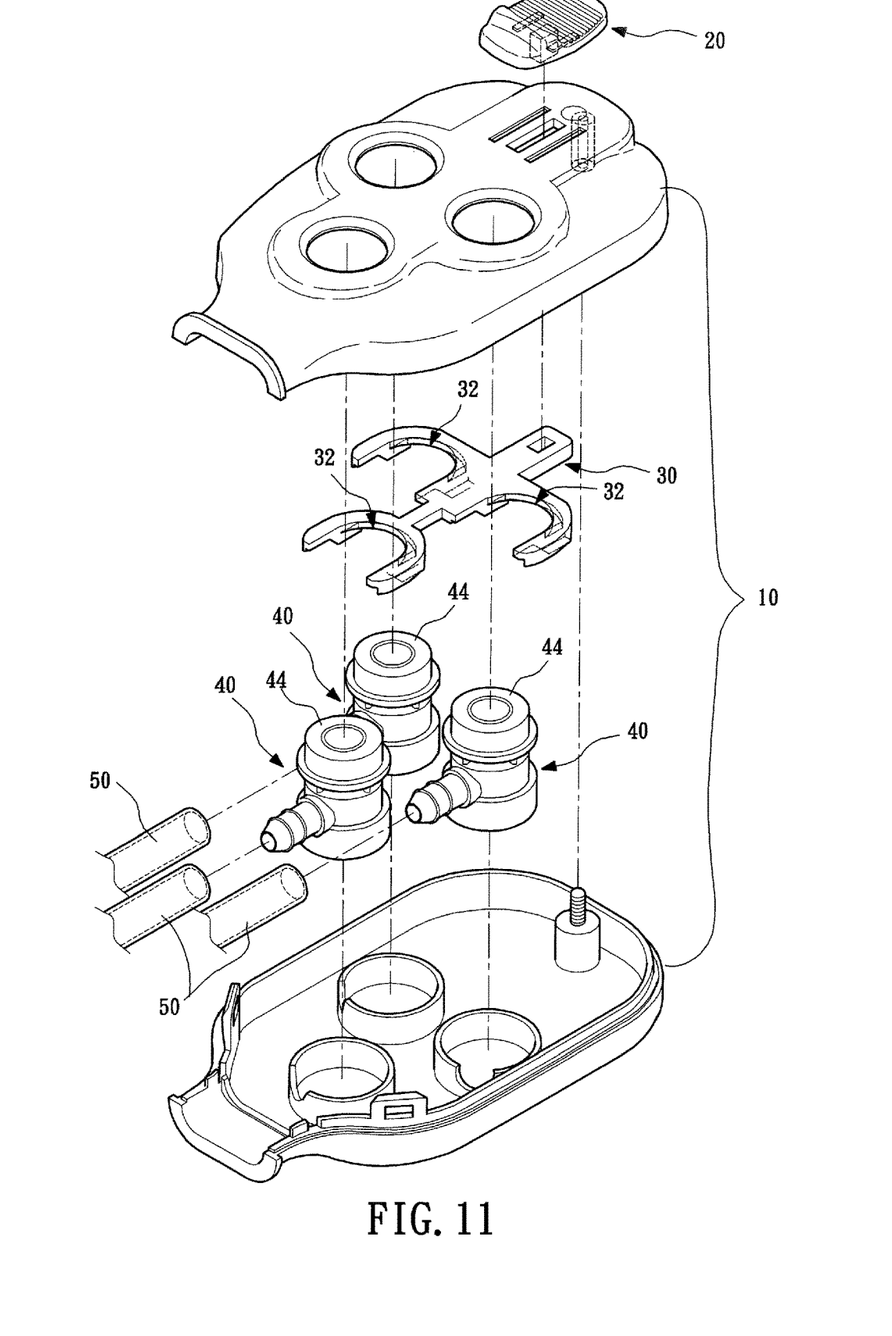
FIG. 11 is an exploded view showing a further embodiment of the present invention.

Referring to FIG. 11, when three such valves 40 are used together, it only needs to change the number of the operation section 32 to three. As such, when the contact member 20 is pushed and moved, the manipulation member 30 can simultaneously press down the switches 44 of the three valves 40.

Figure 12:
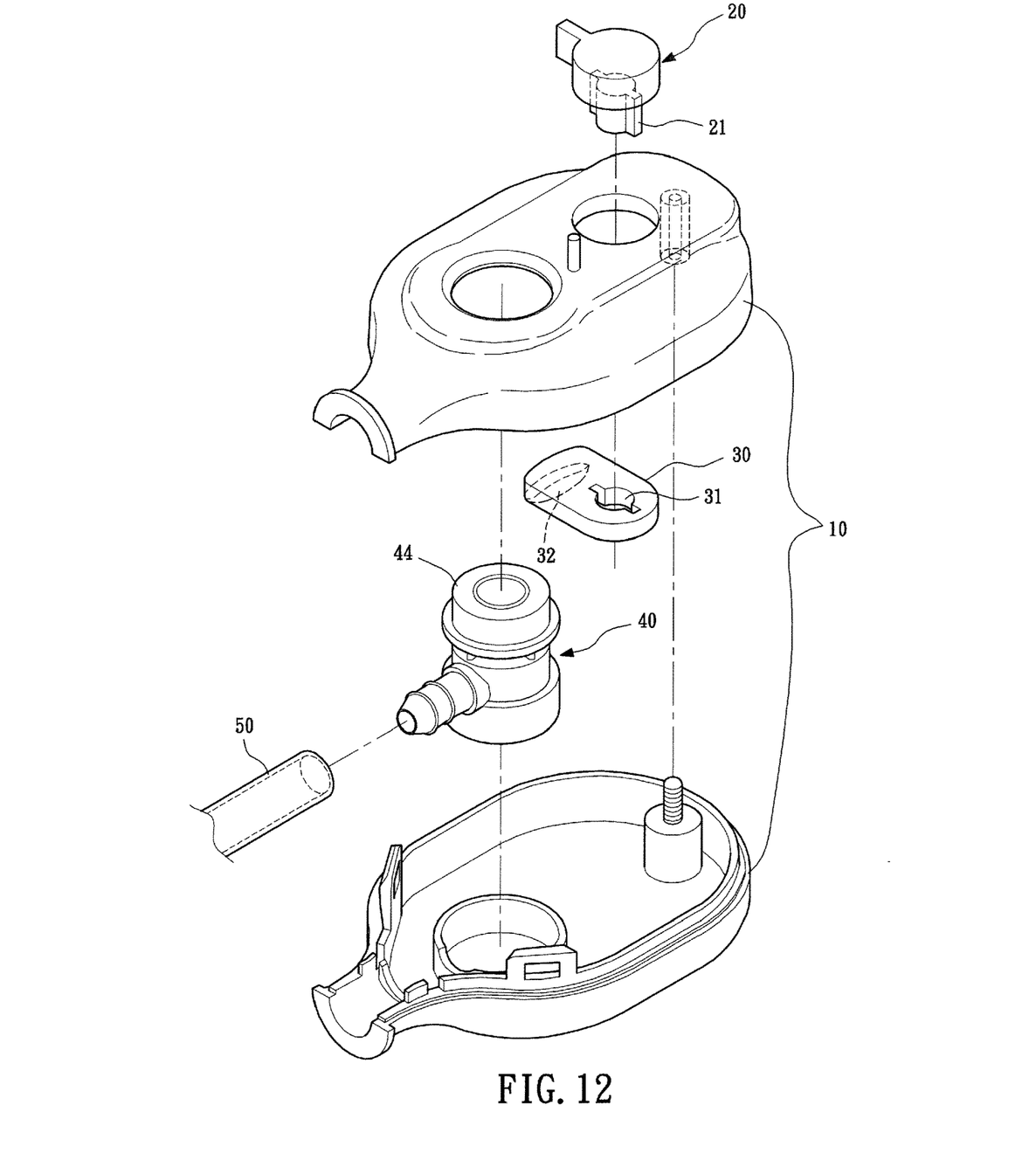
FIG. 12 is an exploded view showing yet a further embodiment of the present invention.
Figure 13:
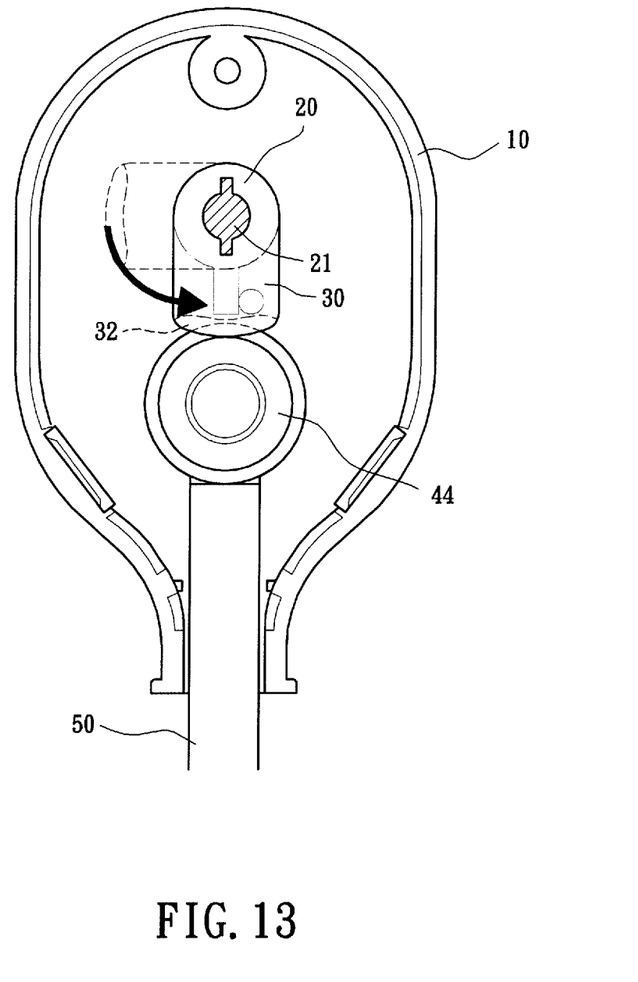
FIG. 13 is a top plan view illustrating a movement of a manipulation member and also showing the interior structure inside the casing of said yet a further embodiment of the present invention.

Referring to FIGS. 12 and 13, the contact member 20 of the present invention can alternatively and rotatably mounted to the casing 10 by a pivot like coupling element 21. The manipulation member 30 can be a plate like member and the operation section 32 is made in the form of an arcuate surface projecting from an underside of the manipulation member 30. As such, rotating the contact member 20 simultaneously causes the manipulation member 30 to rotate in unison therewith and during the rotation of the manipulation member 30, the arcuate surface of the operation section 32 helps reduce the resistance resulting from impact against the circumferential flange of the switch 44 so that the operation section 32 may be easily raised up to reach atop the circumferential flange of the switch 44 for inducing an operation of pressing down the switch 44.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A valve positioning structure for pressing down a switch arranged in a valve so that a fluid is allowed to flow through an inlet opening of the valve when the switch is pressed down in order to control the fluid to flow into/out of at least one bladder, comprising:
    a casing receiving the valve therein;
    a contact member movable on an upper surface of the casing in a first linear direction; and
    a manipulation member movable on a lower surface of the casing, the contact member and the manipulation member being coupled to each other so that the contact member is operable to drive the manipulation member to move, when the manipulation member is driven by the contact member to move toward the switch, the manipulation member has a C-shaped portion with an opening at a side of the C-shaped portion configured to be moved in the first linear direction to receive the switch from the opening and to press down the switch in a second linear direction, substantially perpendicular to the first linear direction, to allow the fluid to flow through the valve, wherein the C-shaped portion has two side parts opposite to each other, between which the switch is received when the manipulation member is moved in the first linear direction toward the switch, wherein each of the side parts has a slope surface configured to move in the first direction over a flange of the switch radially protruding from an annular surface of the switch to press down the flange of the switch in the second linear direction.

2. The valve positioning structure of claim 1, wherein the casing is provided with an inner space receiving the switch.

3. The valve positioning structure of claim 1, wherein the casing is provided with a longitudinal guide hole therein, the contact member comprising a coupling element received in the longitudinal guide hole to have the contact member configured to be moved along the longitudinal guide hole in the first direction and to couple with the manipulation member, whereby the manipulation member is configured to be driven by the contact member to move along the longitudinal guide hole toward the switch in the first direction.

4. The valve positioning structure of claim 1, wherein the casing is provided with multiple longitudinal through holes therein, the contact member comprising multiple guiding elements respectively received in the longitudinal through holes to move along the longitudinal through holes in the first direction.

5. The valve positioning structure of claim 1, wherein the contact member comprises multiple projections thereon to have a finger touch and press the projections.

6. The valve positioning structure of claim 1, wherein the contact member comprises a bearing section thereon to have a finger to contact and push the bearing section.

7. The valve positioning structure of claim 1, wherein said each of the side parts has a horizontal surface extending from a free end thereof, wherein said each of the side parts has its slope surface sloped from its horizontal surface away from its free end.

8. The valve positioning structure of claim 7, wherein the horizontal surface of said each of the side parts is configured to move in the first direction over the flange of the switch.

9. A valve comprising:
    a switch; and
    a manipulation member having a C-shaped portion with an opening at a side of the C-shaped portion configured to be moved in a first linear direction to receive the switch from the opening and to press down the switch in a second linear direction, substantially perpendicular to the first linear direction, to allow a fluid to flow through the valve, wherein the C-shaped portion has two side parts opposite to each other, between which the switch is received when the manipulation member is moved in the first linear direction toward the switch, wherein each of the side parts has a slope surface configured to move in the first direction over a flange of the switch radially protruding from an annular surface of the switch to press down the flange of the switch in the second linear direction.

10. The valve of claim 9 further comprising a contact member configured to drive the manipulation member, wherein the contact member comprises multiple projections thereon for having a finger touch and press the projections.

11. The valve of claim 9 further comprising a contact member configured to drive the manipulation member, wherein the contact member comprises a bearing section thereon to have a finger to contact and push the bearing section.

12. The valve of claim 9, wherein said each of the side parts has a horizontal surface extending from a free end thereof, wherein said each of the side parts has its slope surface sloped from its horizontal surface away from its free end.

13. The valve of claim 12, wherein the horizontal surface of said each of the side parts is configured to move in the first direction over the flange of the switch.

14. The valve of claim 9 further comprising a casing provided with an inner space receiving the switch.

15. The valve of claim 14 further comprising a contact member configured to drive the manipulation member, wherein the casing is provided with a longitudinal guide hole therein, wherein the contact member comprises a coupling element received in the longitudinal guide hole to have the contact member configured to be moved along the longitudinal guide hole in the first direction and to couple with the manipulation member, whereby the manipulation member is configured to be driven by the contact member to move along the longitudinal guide hole toward the switch in the first direction.

16. The valve of claim 14 further comprising a contact member configured to drive the manipulation member, wherein the casing is provided with multiple longitudinal through holes therein, wherein the contact member comprises multiple guiding elements respectively received in the longitudinal through holes to move along the longitudinal through holes in the first direction.

\* \* \* \* \*